United States Patent
Parthasaradhi Reddy et al.

(10) Patent No.: US 9,381,199 B2
(45) Date of Patent: Jul. 5, 2016

(54) LINAGLIPTIN SOLID DISPERSION

(71) Applicants: Bandi Parthasaradhi Reddy, Hyderabad (IN); Kura Rathnakar Reddy, Hyderabad (IN); Dasari Muralidhara Reddy, Hyderabad (IN); Kesireddy Subash Chander Reddy, Hyderabad (IN); Bandi Vamsi Krishna, Hyderabad (IN)

(72) Inventors: Bandi Parthasaradhi Reddy, Hyderabad (IN); Kura Rathnakar Reddy, Hyderabad (IN); Dasari Muralidhara Reddy, Hyderabad (IN); Kesireddy Subash Chander Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 14/589,495

(22) PCT Filed: Jul. 8, 2013

(86) PCT No.: PCT/IN2013/000417
§ 371 (c)(1),
(2) Date: Jan. 5, 2015

(87) PCT Pub. No.: WO2014/009970
PCT Pub. Date: Jan. 16, 2014

(65) Prior Publication Data
US 2015/0290199 A1    Oct. 15, 2015

(30) Foreign Application Priority Data
Jul. 9, 2012    (IN) .............................. 2780/CHE/2012

(51) Int. Cl.
*A61K 31/522*    (2006.01)
*A61K 9/14*    (2006.01)

(52) U.S. Cl.
CPC ............... *A61K 31/522* (2013.01); *A61K 9/146* (2013.01)

(58) Field of Classification Search
CPC .............................. A61K 31/522; A61K 9/14
USPC ..................................................... 514/263.21
See application file for complete search history.

(56) References Cited

U.S. PATENT DOCUMENTS

| | | |
|---|---|---|
| 5,955,475 A | 9/1999 | Krape et al. |
| 7,407,966 B2 | 8/2008 | Dhanoa et al. |
| 2010/0209506 A1 | 8/2010 | Eisenreich |
| 2011/0263617 A1 | 10/2011 | Mark |
| 2012/0046224 A1 | 2/2012 | Karsdal |

FOREIGN PATENT DOCUMENTS

WO    2014009970 A2    1/2014

OTHER PUBLICATIONS

International Written Opinion of PCT/IN2013/000417 dated Jan. 10, 2014.
International Search Report of PCT/IN2013/000417 dated Jan. 10, 2014.

*Primary Examiner* — Golam M M Shameem
(74) *Attorney, Agent, or Firm* — Caesar Rivise, PC

(57) ABSTRACT

The present invention provides a novel amorphous solid dispersion of linagliptin in combination with a pharmaceutically acceptable carrier, process for its preparation and pharmaceutical compositions comprising it.

6 Claims, 1 Drawing Sheet

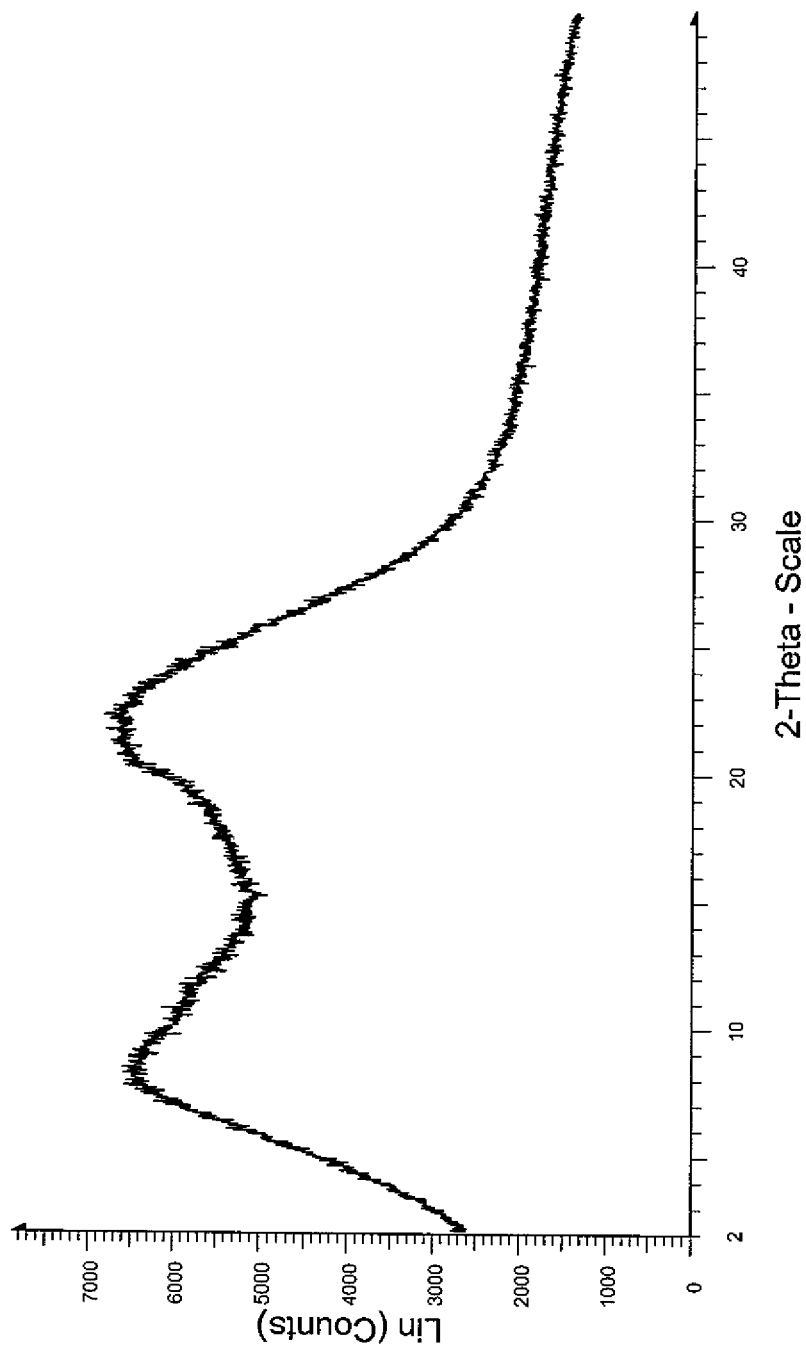

LINAGLIPTIN SOLID DISPERSION

This application is a national stage application of PCT/IN2013/000417 filed Jul. 8, 2013 which claims the benefit of Indian Provisional Patent Application No. 2780/CHE/2012, filed on Jul. 9, 2012, which is incorporated herein by reference.

FIELD OF THE INVENTION

The present invention provides a novel amorphous solid dispersion of linagliptin in combination with a pharmaceutically acceptable carrier, process for its preparation and pharmaceutical compositions comprising it.

BACKGROUND OF THE INVENTION

Linagliptin, chemically 8-[(3R)-3-aminopiperidin-1-yl]-7-(but-2-yn-1-yl)-3-methyl-1-[(4-methylquinazolin-2-yl)methyl]-3,7-dihydro-1H-purine-2,6-dione and has the structure formula:

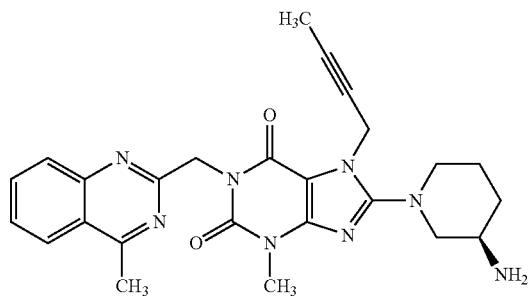 [SMILES: CC#CCn1c(N2CCC[C@@H](N)C2)nc2c1c(=O)n(Cc1nc(C)c3ccccc3n1)c(=O)n2C]

Linagliptin (BI-1356) is a DPP-IV inhibitor. Linagliptin is useful for the prevention or treatment of diabetes mellitus, prediabetes or reduced glucose tolerance. The generic name linagliptin is marketed by BOEHRINGER INGELHEIM under the brand name Tradjenta®.

Linagliptin and its process were disclosed in U.S. Pat. No. 7,407,955.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining one polymorphic Form over the other.

Linagliptin can exist in different polymorphic Forms, which may differ from each other in terms of stability, physical properties, spectral data and methods of preparation.

International application publication no. WO 2007/128721 disclosed Polymorph A, Polymorph B, Polymorph C, Polymorph D, Polymorph E and a mixture of Polymorph A and B of linagliptin.

Amorphous Form of linagliptin was reported in IP.com Journal (2011), 11(9A), 22.

It was observed that the crystalline Forms and amorphous Form of linagliptin either not reproducible or not stable.

We have also found a novel amorphous solid dispersion of linagliptin in combination with a pharmaceutically acceptable carrier. The amorphous solid dispersion of linagliptin is stable, reproducible and so, the amorphous solid dispersion of linagliptin is suitable for formulating linagliptin. Normally amorphous Forms are hygroscopic. Amorphous solid dispersion of linagliptin is found to be non-hygroscopic.

Thus, an object of the present invention is to provide amorphous solid dispersion of linagliptin in combination with a pharmaceutically acceptable carrier, process for its preparation and pharmaceutical compositions comprising it.

SUMMARY OF THE INVENTION

In one aspect, the present invention provides amorphous solid dispersion of linagliptin in combination with a pharmaceutically acceptable carrier.

In another aspect, the present invention there is provided a process for the preparation of amorphous solid dispersion of linagliptin in combination with a pharmaceutically acceptable carrier, which comprises:
  a) preparing a solution comprising a mixture of linagliptin and one or more pharmaceutically acceptable carriers selected from copovidone, ethyl cellulose, hydroxypropyl methylcellulose, polyethylene glycol or soluplus in a solvent; and
  b) removing the solvent to obtain amorphous solid dispersion of linagliptin in combination with a pharmaceutically acceptable carrier.

Yet in another aspect, the present invention provides pharmaceutical compositions comprising a therapeutically effective amount of amorphous solid dispersion of linagliptin along with a pharmaceutically acceptable carrier, and at least one pharmaceutically acceptable excipient.

BRIEF DESCRIPTION OF THE DRAWING

FIG. 1 is a powder X-ray diffractogram patterns of amorphous solid dispersion of linagliptin in combination with a pharmaceutically acceptable carrier.

Powder X-ray diffraction spectrum was measured on a bruker AXS D8 advance powder X-ray diffractometer having a copper-Kα radiation. Approximately 500 mg of sample was gently flattered on a sample holder and scanned from 2 to 50 degrees two-theta, at 0.020 degrees two theta per step and a step time of 1 second. The sample was simply placed on the sample holder. The sample was rotated at 30 rpm at a voltage 40 kV and current 35 mA.

DETAILED DESCRIPTION OF THE INVENTION

The term "room temperature" refers to temperature at about 25 to 35° C.

According to one aspect of the present invention, there is provided amorphous solid dispersion of linagliptin in combination with a pharmaceutically acceptable carrier.

The powdered x-ray diffractogram (PXRD) of amorphous solid dispersion of linagliptin in combination with a pharmaceutically acceptable carrier is shown in FIG. 1.

Amorphous solid dispersion of linagliptin in combination with a pharmaceutically acceptable carrier is found to be stable.

Preferably the pharmaceutically acceptable carriers may be one or more of copovidone, ethyl cellulose, hydroxypropyl methylcellulose, polyethylene glycol or soluplus.

According to another aspect of the present invention, there is provided a process for the preparation of amorphous solid dispersion of linagliptin in combination with a pharmaceutically acceptable carrier, which comprises:
   a) preparing a solution comprising a mixture of linagliptin and one or more pharmaceutically acceptable carriers selected from copovidone, ethyl cellulose, hydroxypropyl methylcellulose, polyethylene glycol or soluplus in a solvent; and
   b) removing the solvent to obtain amorphous solid dispersion of linagliptin in combination with a pharmaceutically acceptable carrier.

Linagliptin used in step (a) may preferably be linagliptin obtained by the known process.

The solvent used in step (a) may preferably be a solvent or a mixture of solvents selected from dimethyl sulfoxide, dimethylacetamide, dimethylformamide, methanol, ethanol, isopropanol, n-butanol and n-pentanol, and more preferably the solvents are dimethyl sulfoxide, dimethylacetamide, dimethylformamide, methanol and ethanol.

Preferably the pharmaceutically acceptable carriers used in step (a) may be selected from copovidone, soluplus or hydroxypropyl methylcellulose.

The solvent may be removed from the solution in step (b) by known methods, for example, distillation or spray drying.

The distillation of the solvent may be carried out at atmospheric pressure or at reduced pressure. The distillation may preferably be carried out until the solvent is almost completely distilled off.

As used herein, "reduced pressure" refers to a pressure of less than 100 mmHg.

According to another aspect of the present invention, there is provided pharmaceutical compositions comprising a therapeutically effective amount of amorphous solid dispersion of linagliptin along with a pharmaceutically acceptable carrier, and at least one pharmaceutically acceptable excipient. The amorphous solid dispersion of linagliptin may preferably be formulated into tablets, capsules, suspensions, dispersions, injectables or other pharmaceutical forms.

The invention will now be further described by the following examples, which are illustrative rather than limiting.

EXAMPLES

Example 1

Preparation of Linagliptin

2-Bromo-1-(but-2-ynyl)-4-methyl-6-((4-methylquinazolin-2-yl)methyl)-1H-imidazo[4,5-b]pyridine-5,7-(4H,6H)-dione (100 gm) was dissolved in dimethylformamide (500 ml) and then added cesium carbonate (180 gm) and (R)-(−)-3-aminopiperidine dihydrochloride (42 gm) at room temperature. The reaction mixture was heated to 120° C. and maintained for 12 hours. The reaction mass was then cooled to room temperature and then added water (1000 ml) and dichloromethane (2000 ml). The layers were separated and the aqueous layer was extracted with dichloromethane. Combined organic layers were dried with sodium sulfate and then concentrated to provide 100 gm of linagliptin.

Example 2

Preparation of Amorphous Linagliptin Solid Dispersion with Hydroxypropyl Methylcellulose A mixture of linagliptin (25 gm) and hydroxypropyl methylcellulose (12.5 gm) was dissolved in ethanol (750 ml) at room temperature. The contents were heated to 70 to 75° C. and filtered through celite bed. The solvent was distilled off under reduced pressure at below 55° C. and then dried to provide 36 gm of amorphous linagliptin solid dispersion with hydroxypropyl methylcellulose.

Example 3

Preparation of Amorphous Linagliptin Solid Dispersion with Hydroxypropyl Methylcellulose Example 2 was repeated using dimethylformamide solvent instead of ethanol solvent to provide amorphous linagliptin solid dispersion with hydroxypropyl methylcellulose.

Example 4

Preparation of Amorphous Linagliptin Solid Dispersion with Hydroxypropyl Methylcellulose Example 2 was repeated using dimethylacetamide solvent instead of ethanol solvent to provide amorphous linagliptin solid dispersion with hydroxypropyl methylcellulose.

Example 5

Preparation of Amorphous Linagliptin Solid Dispersion with Hydroxypropyl Methylcellulose Example 2 was repeated using dimethyl sulfoxide solvent instead of ethanol solvent to provide amorphous linagliptin solid dispersion with hydroxypropyl methylcellulose.

Example 6

Preparation of Amorphous Linagliptin Solid Dispersion with Hydroxypropyl Methylcellulose Example 2 was repeated using methanol solvent instead of ethanol solvent to provide amorphous linagliptin solid dispersion with hydroxypropyl methylcellulose.

Example 7

Preparation of Amorphous Linagliptin Solid Dispersion with Copovidone

A mixture of linagliptin (10 gm) and copovidone (20 gm) was dissolved in ethanol (150 ml) at room temperature. The contents were heated to 65 to 70° C. and filtered through celite bed. The solvent was distilled off under reduced pressure at below 55° C. and then dried to provide 28 gm of amorphous linagliptin solid dispersion with copovidone.

Example 8

Preparation of Amorphous Linagliptin Solid Dispersion with Copovidone

Example 7 was repeated using dimethylformamide solvent instead of ethanol solvent to provide amorphous linagliptin solid dispersion with copovidone.

Example 9

Preparation of Amorphous Linagliptin Solid Dispersion with Copovidone

Example 7 was repeated using dimethylacetamide solvent instead of ethanol solvent to provide amorphous linagliptin solid dispersion with copovidone.

Example 10

Preparation of Amorphous Linagliptin Solid Dispersion with Copovidone

Example 7 was repeated using dimethyl sulfoxide solvent instead of ethanol solvent to provide amorphous linagliptin solid dispersion with copovidone.

Example 11

Preparation of Amorphous Linagliptin Solid Dispersion with Copovidone

Example 7 was repeated using methanol solvent instead of ethanol solvent to provide amorphous linagliptin solid dispersion with copovidone.

Example 12

Preparation of Amorphous Linagliptin Solid Dispersion with Soluplus

A mixture of linagliptin (20 gm) and soluplus (20 gm) was dissolved in ethanol (300 ml) at room temperature. The contents were heated to 70 to 75° C. and filtered through celite bed. The solvent was distilled off under reduced pressure at below 55° C. and then dried to provide 37 gm of amorphous linagliptin solid dispersion with soluplus.

Example 13

Preparation of Amorphous Linagliptin Solid Dispersion with Polyethylene Glycol

A mixture of linagliptin (20 gm) and polyethylene glycol (30 gm) was dissolved in ethanol (500 ml) at room temperature. The contents were heated to 70 to 75° C. and filtered through celite bed. The solvent was distilled off under reduced pressure at below 55° C. and then dried to provide 46 gm of amorphous linagliptin solid dispersion with polyethylene glycol.

Example 14

Preparation of Amorphous Linagliptin Solid Dispersion with Ethyl Cellulose

A mixture of linagliptin (10 gm) and ethyl cellulose (10 gm) was dissolved in ethanol (150 ml) at room temperature. The contents were heated to 70 to 75° C. and filtered through celite bed. The solvent was distilled off under reduced pressure at below 55° C. and then dried to provide 18 gm of amorphous linagliptin solid dispersion with ethyl cellulose.

Example 15

Preparation of Amorphous Linagliptin Solid Dispersion with Copovidone

2-Bromo-1-(but-2-ynyl)-4-methyl-6-((4-methylquinazolin-2-yl)methyl)-1H-imidazo[4,5-b]pyridine-5,7-(4H,6H)-dione (100 gm) was dissolved in dimethylformamide (500 ml) and then added cesium carbonate (180 gm) and (R)-(−)-3-aminopiperidine dihydrochloride (42 gm) at room temperature. The reaction mixture was heated to 120° C. and maintained for 12 hours. The reaction mass was then cooled to room temperature and then added water (1000 ml) and dichloromethane (2000 ml). The layers were separated and the aqueous layer was extracted with dichloromethane. Combined organic layers were dried with sodium sulfate and then added copovidone (200 gm) and ethanol (1500 ml) at room temperature. The contents were heated to 65 to 70° C. and filtered through celite bed. The solvent was distilled off under reduced pressure at below 55° C. and then dried to provide 285 gm of amorphous linagliptin solid dispersion with copovidone.

Example 16

Preparation of Amorphous Linagliptin Solid Dispersion with Hydroxypropyl Methylcellulose 2-Bromo-1-(but-2-ynyl)-4-methyl-6-((4-methylquinazolin-2-yl)methyl)-1H-imidazo[4,5-b]pyridine-5,7-(4H,6H)-dione (100 gm) was dissolved in dimethylformamide (500 ml) and then added cesium carbonate (180 gm) and (R)-(−)-3-aminopiperidine dihydrochloride (42 gm) at room temperature. The reaction mixture was heated to 120° C. and maintained for 12 hours. The reaction mass was then cooled to room temperature and then added water (1000 ml) and dichloromethane (2000 ml). The layers were separated and the aqueous layer was extracted with dichloromethane. Combined organic layers were dried with sodium sulfate and then added hydroxypropyl methylcellulose (50 gm) and ethanol (3000 ml) at room temperature. The contents were heated to 70 to 75° C. and filtered through celite bed. The solvent was distilled off under reduced pressure at below 55° C. and then dried to provide 145 gm of amorphous linagliptin solid dispersion with hydroxypropyl methylcellulose.

We claim:
1. An amorphous solid dispersion of linagliptin in combination with one or more pharmaceutically acceptable carriers, wherein the one or more pharmaceutically acceptable carriers is selected from the group consisting of copovidone, ethyl cellulose, hydroxypropyl methyl cellulose, polyethylene glycol, and soluplus.

2. The amorphous solid dispersion as claimed in claim 1, having a powder X-ray diffractogram as shown in FIG. 1.

3. A process for the preparation of amorphous solid dispersion of linagliptin in combination with a pharmaceutically acceptable carrier of claim 1, which comprises: a. preparing a solution comprising a mixture of linagliptin and one or more pharmaceutically acceptable carriers selected from copovidone, ethyl cellulose, hydroxypropyl methylcellulose, polyethylene glycol or soluplus in a solvent; and b. removing the solvent to obtain amorphous solid dispersion of linagliptin in combination with a pharmaceutically acceptable carrier.

4. The process as claimed in claim 3, wherein the solvent used in step (a) is a solvent or a mixture of solvents selected from dimethyl sulfoxide, dimethylacetamide, dimethylformamide, methanol, ethanol, isopropanol, n-butanol and n-pentanol.

5. The process as claimed in claim 4, wherein the solvents are dimethyl sulfoxide, dimethylacetamide, dimethylformamide, methanol and ethanol.

6. The process as claimed in claim 3, wherein the pharmaceutically acceptable carriers used in step (a) is selected from copovidone, soluplus or hydroxypropyl methylcellulose.

* * * * *